United States Patent [19]

Mikkelsen

[11] Plant 4,207

[45] Feb. 7, 1978

[54] KALANCHOE PLANT

[75] Inventor: James C. Mikkelsen, Ashtabula, Ohio

[73] Assignee: Mikkelsens, Inc., Ashtabula, Ohio

[21] Appl. No.: 766,579

[22] Filed: Feb. 8, 1977

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Donald D. Jeffery

[57] ABSTRACT

A kalanchoe cultivar having an unusually thick and upright main stem bearing golden orange flowers which stay open at night.

1 Drawing Figure

The present invention relates to a new and distinctive cultivar of kalanchoe plant, botanically known as kalanchoe and known by the cultivar name Nugget. The new cultivar was developed by me through controlled breeding by crossing the cultivar Gelbe Melody, disclosed in U.S. Plant Pat. No. 3,854, issued Mar. 30, 1976 to Adolf Grob, (seed parent) with the cultivar Saturn, disclosed in U.S. Plant Pat. No. 3,852, issued Mar. 30, 1976 to Adolf Grob. Asexual reproduction of the new cultivar by stem cuttings has shown that the unique features of this new kalanchoe are stabilized and are reproduced true to type in successive propagations.

The following characteristics distinguish the new kalanchoe from both its parent cultivars and other cultivated kalanchoes of this type known and used in the floriculture industry:

1. Vigorous, strong upright growth showing resemblance to the cultivar Gelbe Melody. The main stem is unusually thick and upright.

2. Excellent branching occurs with the removal of the apical tip or when flowering is induced. Side shoots develop at nearly every node while in Gelbe Melody branching is mostly predominant in the area of the top two to four nodes.

3. Cutting production is double that of Gelbe Melody or Saturn in the same period of time. Propagation of stem cuttings is faster and more uniform than for either parent.

4. Flower color is a sharp golden orange color as compared to the yellow flower color of Gelbe Melody. The flower color of Nugget is a lighter orange than the flowers of Saturn, and also lighter than the orange red colos of Rotkappchen or Sirius. The cultivar Rotkappchen is disclosed in U.S. Plant Pat. No. 3,851, issued Mar. 30, 1976 to Adolf Grob and the cultivar Sirius is disclosed in pending application Ser. No. 709,282, filed July 27, 1976 in the name of Adolf Grob.

5. Flowers are supported on strong vigorous stems. Flowering is a week later than Gelbe Melody or Saturn, being approximately 11 weeks in summer and 12 weeks in winter.

6. The foliage is compact and small, resembling the appearance of Gelbe Melody but having much closer and compact internodes.

7. Selection of Nugget for commercialization was also made on the basis that the flowers of this cultivar do not typically close at night as do many kalanchoes.

The accompanying colored photograph illustrates the overall appearance of the cultivar, and shows the colors as true as it is reasonably possible to obtain in a colored reproduction of this type.

The following is a detailed description of my new kalanchoe cultivar based on plants produced under commercial practices in the greenhouses of Mikkelsens Inc., Ashtabula, Ohio, with the plants being grown in 10 cm. plastic pots from unrooted cuttings stuck directly into the pot on August 25 and given short day treatment on September 16. The plant was not pinched, was grown on a capillary mat and was in flower on December 13th. Color references are made to the Royal Horticultural Society Colour Chart except where general terms of ordinary dictionary significance are used.

Parentage: A controlled pollination of Gelbe Melody as the seed parent crossed with Saturn as the pollen parent.

Propagation:

*Type cutting.*—Two cm. long cuttings.

*Time to visible rooting.*—10–12 days at 21° C summer, and 12–15 days at 21° C winter.

*Rooting habit.*—Rapid, profuse, dendritic.

Plant description:

*Form.*—Upright, semi-compact. When grown under the above conditions, the plant is approximately 20 cm. high by 20 cm. in diameter, an excellent combination. Side shoots are 10–12 cm. long. The basal stem diameter is 12–14 mm. in diameter.

*Habit of growth.*—Rapid, vigorous, upright with prolific side branching.

*Foliage.*—Plentiful, durable and nicely compliments the excellent placement of the flowers. Size: 8 cm. wide by 9 cm. long; 2 cm. petiole, some twisting, generally concave upwards. Shape: Nearly ovate, apice obtuse to rounded, base obtuse. Texture: Glabrous, coriaceous. Margin: Crenate. Color: Mature foliage, top side between yellow green 147A-Green 137A, underside yellow green 147B.

Flower description

*Flowering habits.*—Multiple inflorescence occurring on the terminal, and lateral side shoots are compound paniculate cyme. Central or crown flower opening first followed sequentially by developing secondary flowers.

*Natural flowering season.*—End of December thru early January. Flowering time under controlled day length at 20° C in summer is 11 weeks; in winter is 12 weeks. Flowers are long lasting so that the total inflorescence is well displayed before deterioration begins.

*Flower bud.*—Elliptical, covered with four green sepals, elongating to tubular as flower matures, total length of corolla 15–16 mm.

*Flowers borne.*—Each inflorescense is born on sturdy, vigorous peduncles. The individual flower pedicels are strong, rigid.

*Quantity of flowers.*—The terminal inflorescence may have 30 or more flowers and 6 to 8 lower side shoots with additional flowers. Lateral shoots may likewise have 30 or more flowers and lesser amounts of small side shoots. Highly floriferous.

*Petals.*—Shape: Joined, tubular neck, terminally nearly circular with pointed apice. Color: Top side when opening orange red 30B-C, fading to 30D; under side 29A. Number of petals: Four, approximately 7–8 mm. in diameter, total flower 15–16 mm. in diameter.

*Reproductive organs.*—Stamens: 8 in number. Anther shape: Flat; color yellow. Filament color: Translucent green. Pollen color: Yellow Pistels:

Stigma shape: Flat, crystalline: translucent white in color. Style color: Light green. Ovaries: Four in number; size 5–6 mm.; color yellow green, 151A.

Disease resistance: As of the present time, there are no signs of powdery mildew when grown in the presence of other kalanchoes infected with common mildew. Foliage and stems appear to be resistant to botrytis.

To summarize, the new cultivar has an overall crisp, clean, well proportioned and attractive appearance with excellent placement of high quality flowers.

I claim:

1. A new and distinct cultivar of kalanchoe plant known by the cultivar name Nugget and characterized particularly as to novelty by the combined characteristics of vigorous, strong, upright growth; excellent branching; capable of superior cutting production, and fast and uniform propagation; sharp, golden orange flower color, with the flowers being supported on strong stems; and compact and small foliage.

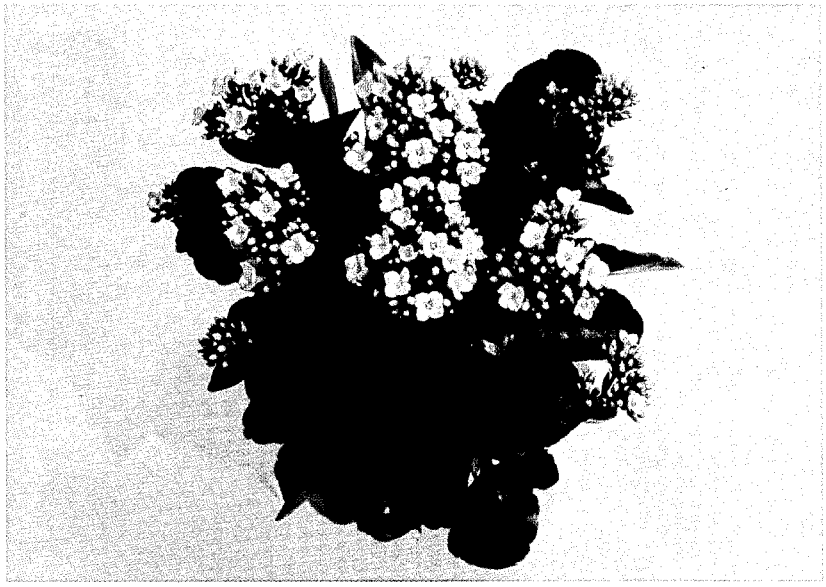

* * * * *